US00PP08017P

United States Patent [19]

Drewlow

[11] Patent Number: Plant 8,017

[45] Date of Patent: Oct. 27, 1992

[54] POINSETTIA PLANT NAMED PINK YULETIDE

[75] Inventor: Lyndon W. Drewlow, Ashtabula, Ohio

[73] Assignee: Mikkelsens, Inc., Ashtabula, Ohio

[21] Appl. No.: 668,605

[22] Filed: Mar. 13, 1991

[51] Int. Cl.[5] ..... A01H 5/00
[52] U.S. Cl. ..... Plt./86.3
[58] Field of Search ..... Plt./86, 863

[56] References Cited

U.S. PATENT DOCUMENTS

Plt. 3,721 5/1975 Murison ..... Plt. 86

*Primary Examiner*—Howard J. Locker
*Attorney, Agent, or Firm*—Foley & Lardner

[57] ABSTRACT

A new Poinsettia plant named Pink Yuletide particularly characterized by its pink bracts, development of full length shoots, relatively light green leaves, tolerance to low light and high temperatures in home environment, medium sized bracts, early flowering, relatively small, non-splitting cyathia which are retained under stress conditions, and relatively short growth habit.

1 Drawing Sheet

The present invention comprises a new and distinctive cultivar of Poinsettia plant, botanically known as *Europhobia pulcherrima*, and referred to by the cultivar name Pink Yuletide.

The new cultivar was created beginning with the discovery of a pink color sport of Merrimaker, disclosed in U.S. Plant Pat. No. 6,097. The sport was discovered growing among plants of Merrimaker in a cultivated area, and was recognized by its pink color, compared to the red bracts of Merrimaker.

The pink sport was subsequently grafted to the excellent branching type cultivar Fantastic (not patented) in an attempt to transfer to the new cultivar the branching habit of Fantastic while retaining the pink flower color of the sport. The graft was successful, resulting in the new cultivar Pink Yuletide which has the excellent branching habits of Fantastic while retaining the bract quality and color of the pink sport of Merrimaker.

Asexual reproduction of the new cultivar by stem cuttings as performed in Ashtabula, Ohio has shown that the unique features of this new Poinsettia are stabilized and are reproduced true to type in successive propagations.

The following characteristics distinguish Pink Yuletide from Merrimaker and Fantastic (known formally as 'Mikkel Fantastic', U.S. Plant Pat. No. 3,721), and also from other cultivated Poinsettia of this type known and used in the floriculture industry.

1. When five or more nodes are left after a pinch (apical tip removal), Pink Yuletide develops full length shoots from each node like Fantastic, while the pink sport of Merrimaker and Merrimaker develop a full length shoot from only the upper two or three nodes, with the balance of shoots staying repressed.
2. Pink Yuletide plants at 20 to 22 cm are shorter than plants of the pink sport of Merrimaker plants (at 24 to 26 cm) when similar sized plants are left after pinching because there is little or no apical dominance in the branched types. Thus, all shoots develop to the same height instead of two or three shoots becoming dominant. Fantastic is taller (at 28 to 30 cm) than Pink Yuletide, even though it branches from each node.

3. Pink Yuletide has slightly lighter green leaves than the pink sport of Merrimaker and Fantastic, but all would be classified as 137A on the R.H.S. Color Chart.
4. Bract coloration of Pink Yuletide and the pink sport of Merrimaker are similar in color, ranging from 52A on newly expanded bract leaves through 54B to 54C on edge of older bracts. The smaller Fantastic bract is mostly 52A.
5. Pink Yuletide is more tolerant to low light levels and high temperature conditions of the average home as its leaves do not yellow and drop like the pink sport of Merrimaker and Merrimaker. Under these conditions, when kept moist, foliage retention of Pink Yuletide is excellent, similar to Fantastic.
6. Pink Yuletide has a smaller cyathia (cluster of flowers in the center of the bract) than the pink sport of Merrimaker.
7. Pink Yuletide has a similar sized bract at 25 to 30 cm in diameter to the pink sport of Merrimaker, while Fantastic has a 20 to 25 cm bract and is not as full as Pink Yuletide and the pink sport of Merrimaker.
8. Pink Yuletide is less susceptible to heat delay of flower bud initiation under night temperatures above 21° C., being similar in this regard to the pink sport of Merrimaker, while Fantastic heat delays under these temperatures.
9. All other characteristics of Pink Yuletide are similar to the pink sport of Merrimaker, such as early flower initiation under natural short days, no sign of epinasty (leaf petiole twisting), similar shaped leaves and bracts, retention of cyathia under stress conditions, and non-splitting cyathia.

The accompanying colored photograph illustrates in front perspective view the overall appearance of Pink Yuletide, showing the colors as true as it is reasonably possible to obtain in a colored reproduction of this type. The photograph was taken on Dec. 20, 1989 under double poly greenhouse covering on an overcast day in Ashtabula, Ohio.

The following is a detailed description of my new cultivar based on plants produced in Ashtabula, Oh.

during the fall season of the year. Plants were grown in 15 cm pots, and measurements were taken 15 weeks after rooted cuttings were planted. Height measurements were taken from the soil line of the container with one application of 1500 ppm CCC growth regulator in week 39 to Pink Yuletide and all comparison cultivars. The plants were grown at 64°-68° F. night temperatures under 3500-4000 foot candles of light, and 300 ppm Nitrogen, 150 ppm Potassium and 300 ppm Phosphorous nutritional levels with trace elements added. Habit of growth, foliage coloration, leaf variegation, size of leaves and flower size will be influenced by nutritional and environmental conditions. Color references are made to The Royal Horticultural Society Colour Chart except where general terms of ordinary dictionary significance are used.

Parentage: Pink non-branching sport of Merrimaker grafted with branching type cultivar Fantastic.

Propagation:

(A) *Type cutting.*—Stem, 5 to 6 cm long.

(B) *Time to root.*—14 days at 21° C. summer, 18 days at 21° C. winter.

(C) *Rooting habit.*—Abundant, fibrous roots.

Plant description: Habit of growth, foliage coloration and size of leaf will be greatly influenced by nutritional and environmental conditions, thus data that follows was taken from plants grown under the conditions stated above.

(A) *Form.*—Upright; when apical meristem is removed (pinching) leaving 5 or more nodes above the soil line of pot, generally all lateral shoots will emerge and develop.

(B) *Habit of growth.*—Strong, thick stems that hold the bracts up for good flower display. Growth is vigorous, and depending on scheduling system used, plants may need an application of a chemical growth regulator such as Cycocel (CCC). Nodal connection of stems are strong enough to hold up bracts without breaking.

(C) *Foliage description.*—Leaves are alternate and borne on 5-6 cm long petioles that are yellow-green in color. (1) Size: Mature leaves are 13 to 15 cm long by 9 to 10 cm wide at broadest area. (2) Shape: Leaf shape is variable from ovate to hastate with an acute apex and rounded base. (3) Texture: Upper surface glabrous, lower surface glabrous and rugose because of protruding veins. (4) Margin: Entire, but some leaves are large lobed. (5) Color: Young foliage, top side 144A, under side 144A; mature foliage, top side 137A, under side 137C. (6) No epinasty from low levels of ethylene when boxed for up to 5 days.

Flowering description: Cyathia.

(A) *Flowering habits.*—Earlier flowering than most commercial cultivars, apparently having a longer critical day length for flower initiation. Under controlled day length, development time is approximately 10 weeks. Flowers earlier, like pink mutation of Merrimaker, than most commercial cultivars under natural day length in Ohio, but takes approximately the same time to develop when tested under exact controlled day lengths with other commercial cultivars. The characteristic of earlier flower initiation is of commercial significance. Involucre is almost flat with only slight reflexing.

(B) *Natural flowering season.*—November 15 to 25 under Ohio conditions.

(C) *Cyathia description.*—Are very stress tolerant, remaining in the involucre for a considerable time under low fertility, low light, high temperature conditions; severe drying may cause them to drop. Most have two nectar cups.

(D) *Cyathia borne.*—Stay closely clustered for a considerable time without growing apart (splitting). Flowering can be initiated any time of the year by controlling day length; cyathia will continue to initiate until day length is greater than approximately 13 hours.

(E) *Quantity of cyathia.*—Is highly dependent on cultural practices and varies from minimum of 8 to 10 to as many as 50; cyathia will continue to develop from November to April resulting in the large number.

(F) *Bracts.*—Last true leaves will show a pinkish cast. (1) Shape: Ovate; mature 10 to 12 cm long and 8 to 9 cm wide on a pinched plant; petioles 1.5 cm long. (2) Color at maturity: 54B fading to 54C at edge of bract; young bract 52A; under side 51D. (3) Number of bracts: Up to 50 or more depending on growing conditions, with 20-25 normal number. Bract size varies with growing conditions, pinching, and use of growth regulators.

(G) *Reproductive organs.*—(1) Stamens: Numerous. (a) Anther shape: Oblong, yellow in color with red tint. (b) Filament color: Pink-red. (c) Pollen color: Yellow. (2) Pistils: (a) Stigma shape: Forked, reddish-pink in color. (b) Style color: Whitish green. (c) Ovaries: 3 celled, 3 mm, yellow green when stigma receptive. (3) Nectar cups: 1 or 2 on each cyathia; yellow in color with tint of red; nectar is usually readily available on maturing cyathia.

Disease resistance: Appears to be somewhat resistant to white fly which prefer other cultivars over Pink Yuletide; otherwise has shown no disease problems to date.

I claim:

1. A new and distinct cultivar of Poinsettia plant named Pink Yuletide, as illustrated and described.

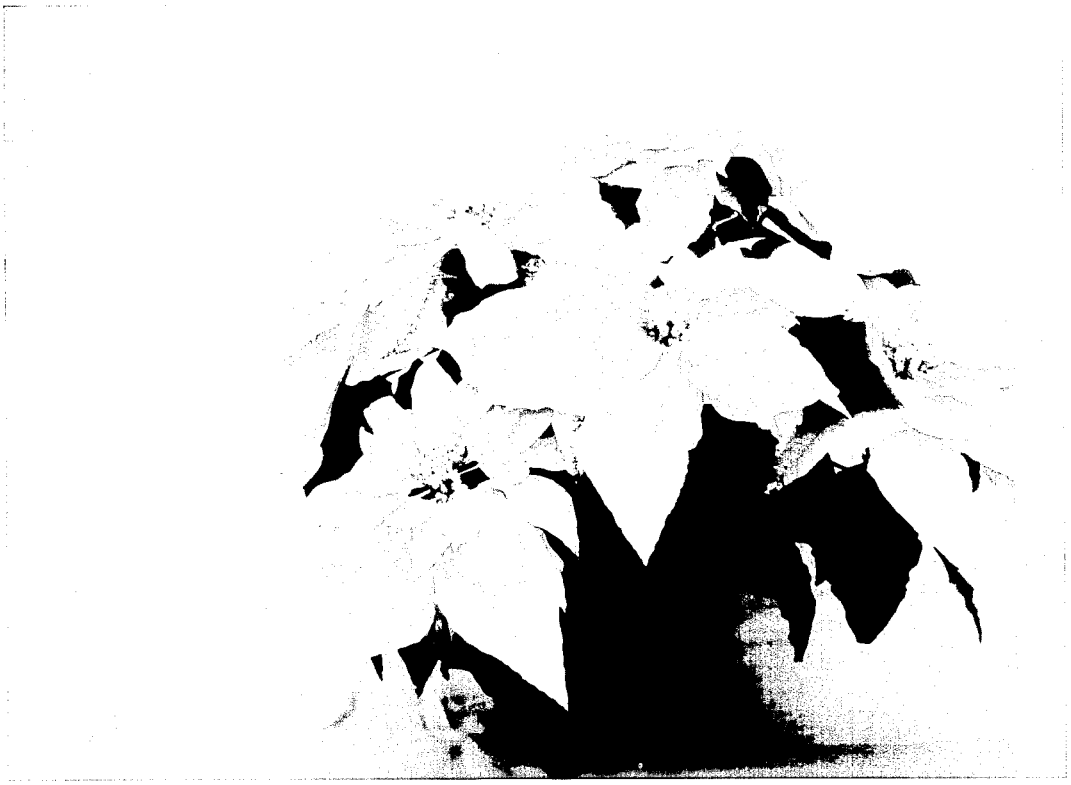

* * * * *